(12) United States Patent
Granet et al.

(10) Patent No.: US 11,857,454 B2
(45) Date of Patent: *Jan. 2, 2024

(54) OSTOMY FACEPLATES CONFIGURED FOR USE IN CLOSE PROXIMITY WITH CREASES, ROLLS, OR FOLDS

(71) Applicant: Sanguine Technology, LLC, Dunmore, PA (US)

(72) Inventors: Rosemary Granet, Scranton, PA (US); Paul Jason Granet, Scranton, PA (US); Gregory M. Murphy, Rancho Palos Verdes, CA (US)

(73) Assignee: Sanguine Technology, LLC, Scranton, PA (US)

(*) Notice: Subject to any disclaimer, the term of this patent is extended or adjusted under 35 U.S.C. 154(b) by 269 days.

This patent is subject to a terminal disclaimer.

(21) Appl. No.: 17/367,379

(22) Filed: Jul. 4, 2021

(65) Prior Publication Data
US 2023/0000662 A1 Jan. 5, 2023

(51) Int. Cl.
*A61F 5/448* (2006.01)
(52) U.S. Cl.
CPC .................................. *A61F 5/448* (2013.01)
(58) Field of Classification Search
CPC .......... A61F 5/445; A61F 5/443; A61F 5/448; A61F 5/4404; A61F 2013/0057; A61F 2013/00978; A61F 2005/4483; A61F 5/44; A61M 1/915; A61M 27/00; A61M 1/90; A61M 1/916; A61M 1/984; B65D 41/16; B65D 41/165; B65D 41/17; B65D 41/18; B65D 41/46; B65D 41/465; B65D 41/47; B65D 41/48; B65D 41/485; B65D 43/0204; B65D 43/0206; B65D 43/0208; B65D 43/021; B65D 43/0212; B65D 45/30; B65D 47/127

See application file for complete search history.

(56) References Cited

U.S. PATENT DOCUMENTS

| | | | | |
|---|---|---|---|---|
| 3,980,213 | A * | 9/1976 | Ramsay | B65D 47/127 222/570 |
| 6,537,261 | B1 * | 3/2003 | Steer | A61F 5/448 604/342 |
| 7,891,514 | B1 * | 2/2011 | Walsh | B65D 43/0212 220/780 |
| 9,204,990 | B1 * | 12/2015 | Berven | A61F 5/443 |
| 9,750,633 | B1 * | 9/2017 | Follenius | A61F 5/443 |
| 2003/0015532 | A1 * | 1/2003 | Rickman | E04F 21/00 220/780 |
| 2011/0137271 | A1 * | 6/2011 | Andresen | A61F 13/023 604/319 |

(Continued)

*Primary Examiner* — Adam Marcetich
(74) *Attorney, Agent, or Firm* — Landmark Intellectual Property Law, LLC; Gregory M Murphy

(57) ABSTRACT

In general, the present invention is directed to systems and methods for providing ostomy faceplates configured to be positioned in close proximity to an incision, roll, crease, or fold. Embodiments of the present invention may include an ostomy appliance or faceplate with a non-circular flange for attachment of a bag or pouch. In accordance with some embodiments of the present invention, the non-circular flange may include at least one substantially straight edge. The substantially straight edge may comprise a single line, or multiple lines or curves.

9 Claims, 8 Drawing Sheets

(56) References Cited

U.S. PATENT DOCUMENTS

| | | | |
|---|---|---|---|
| 2011/0166539 A1* | 7/2011 | Eakin | A61F 5/445 604/339 |
| 2011/0278253 A1* | 11/2011 | Goodall | B65D 41/0414 215/200 |
| 2012/0123363 A1* | 5/2012 | Grum-Schwensen | A61F 5/448 604/342 |
| 2012/0253302 A1* | 10/2012 | Corley | A61M 1/86 604/319 |
| 2018/0289185 A1* | 10/2018 | Oakes | B65D 21/0223 |
| 2020/0253777 A1* | 8/2020 | Jones | A61F 5/443 |
| 2021/0161725 A1* | 6/2021 | Edwards | A61F 13/0216 |
| 2022/0168131 A1* | 6/2022 | Heckler | A61F 5/443 |
| 2023/0130212 A1* | 4/2023 | Avis | B01D 53/9418 502/65 |

* cited by examiner 1110
1130
1120

1210
1230
1220

OSTOMY FACEPLATES CONFIGURED FOR USE IN CLOSE PROXIMITY WITH CREASES, ROLLS, OR FOLDS

RELATED APPLICATIONS

This application is a continuation-in-part of, and claims priority to, U.S. patent application Ser. No. 16/849,909 filed on 15 Apr. 2020, entitled "Systems and Methods for Providing Ostomy Faceplate in Close Proximity with Negative Pressure Wound Devices," which claims priority to U.S. Provisional Patent Application No. 62/871,670, filed on 08 Jul. 2019 and entitled "Ostomy Appliance," which is incorporated by reference herein in its entirety.

BACKGROUND

Ileostomies (stomas made from the last portion of the small intestine) are generally placed in the lower right quadrant of a patient's abdominal wall below the level of the umbilicus but above the level of the pubic hair. Colostomies (stomas made from part of the large intestine) are generally placed in the lower left quadrant of the abdomen, although they can be placed in other locations. However, the site selection of an ostomy is often restricted, as stomas should be sited within margins of the rectus abdominal muscle, which runs vertically and in front of the abdomen. Placing a stoma within the margins of this muscle may help prevent later complications, such as parastomal hernias.

In order to avoid any potential unwanted leakage, it can be important for an ostomy appliance, or faceplate, to tightly seal against a patient's or user's skin. Removable adhesive is generally used to provide a secure fit. However, some patients or users have creases, folds, or rolls in their skin that may impact the fit of the ostomy appliance or faceplate. For example, due to biological constraints discussed above, and ostomy may be placed close to where a patient's or user's abdominal fat creases or folds—particularly when the patient or user is leaning forward.

Such creases, rolls, and folds may cause repeated folding of the skin under the ostomy appliance or faceplate, potentially gradually reducing the seal of the appliance or faceplate against a patient's or user's skin.

Accordingly, it is desirable to provide an ostomy appliance that can be used in as close as possible to a patient's or user's skin creases, folds, or rolls to provide a more secure connection to the skin.

SUMMARY OF THE INVENTION

Some aspects of the present invention, in accordance with some embodiments, may comprise ostomy appliance or faceplate with a non-circular flange for attachment of a bag or pouch. In general, the present invention is directed to systems and methods for providing ostomy faceplates configured to be positioned in close proximity to an incision, roll, crease, or fold. Embodiments of the present invention may include an ostomy appliance or faceplate with a non-circular flange for attachment of a bag or pouch. In accordance with some embodiments of the present invention, the non-circular flange may include at least one substantially straight edge. The substantially straight edge may comprise a single line, or multiple lines or curves.

These and other aspects will become apparent from the following description of the invention together with the following drawings, although variations and modifications may be effectuated without departing from the scope of the novel concepts of the invention.

BRIEF DESCRIPTION OF THE DRAWINGS

The present invention can be more fully understood by reading the following detailed description together with the accompanying drawings, in which like reference indicators are used to designate like elements. The accompanying figures depict certain illustrative embodiments and may aid in understanding the following detailed description. Before any embodiment of the invention is explained in detail, it is to be understood that the invention is not limited in its application to the details of construction and the arrangements of components set forth in the following description or illustrated in the drawings. The embodiments depicted are to be understood as exemplary and in no way limiting of the overall scope of the invention. Also, it is to be understood that the phraseology and terminology used herein is for the purpose of description and should not be regarded as limiting. The detailed description will make reference to the following figures, in which.

Figure 1:
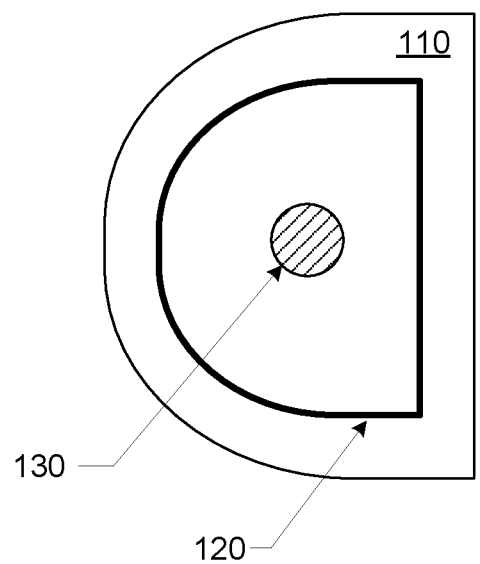
FIG. 1 depicts an exemplary "D"-shaped ostomy appliance with "D"-shaped flange, in accordance with some embodiments of the present invention.

Before any embodiment of the invention is explained in detail, it is to be understood that the present invention is not limited in its application to the details of construction and the arrangements of components set forth in the following description or illustrated in the drawings. The present invention is capable of other embodiments and of being practiced or being carried out in various ways. Also, it is to be understood that the phraseology and terminology used herein is for the purpose of description and should not be regarded as limiting.

DETAILED DESCRIPTION

The matters exemplified in this description are provided to assist in a comprehensive understanding of various exemplary embodiments disclosed with reference to the accompanying figures. Accordingly, those of ordinary skill in the art will recognize that various changes and modifications of the exemplary embodiments described herein can be made without departing from the spirit and scope of the claimed invention. Descriptions of well-known functions and constructions are omitted for clarity and conciseness. Moreover, as used herein, the singular may be interpreted in the plural, and alternately, any term in the plural may be interpreted to be in the singular.

The present invention sets forth an ostomy appliance and/or system that may include one or more of several features, including but not limited to the following: having a straight edge or substantially straight edge of a flange that may be aligned with a patient's or user's skin crease, roll, or fold.

In accordance with some embodiments (and as discussed in greater detail below), the design may comprise a straight edge or substantially straight edge as part of an ostomy faceplate or appliance. The straight or substantially straight end of the faceplate or appliance may include a tapered end, may comprise different adhesive than the overall appliance or faceplate, and/or may be made from or comprised of a different material.

The present document uses the term "flange," which is intended to refer to a physical component that assists in the connection between a faceplate or appliance and a bag or pouch. Note that while the present invention generally illustrates faceplates and appliances as being separate from the bag or pouch, one-piece appliance-and-pouch devices are also contemplated. In such combined devices, there is still a flange that provides connection between the bag and the faceplate or appliance—though in combined devices the bag or pouch may not be removable.

With reference to FIG. 1, a substantially "D" shaped ostomy appliance is illustrated. The appliance in FIG. 1 comprises a material 110 that is generally attached to, or adhered to, a patient, and may comprise a flexible and comfortable material, such as flexible wound dressing (for example, DUODERM®—manufactured for ConvaTec). Flange 120 may comprise a more rigid (though still flexible and bendable) ring that may encircle an orifice 130. During use, the orifice 130 may be aligned with a user's or patient's stoma. A bag or pouch may be attach to the flange 120 to receive effluent from the stoma.

Note that the present invention provides a means to locate an ostomy faceplate or appliance close to user's skin creases, rolls, or folds. The general shape of the outside portion of the appliance can be of any variety, as at least one goal of the invention is to get as close to the crease, roll, or fold by positioning the straight or substantially straight edge of the flange proximate to the crease, roll, or fold.

Figure 2:
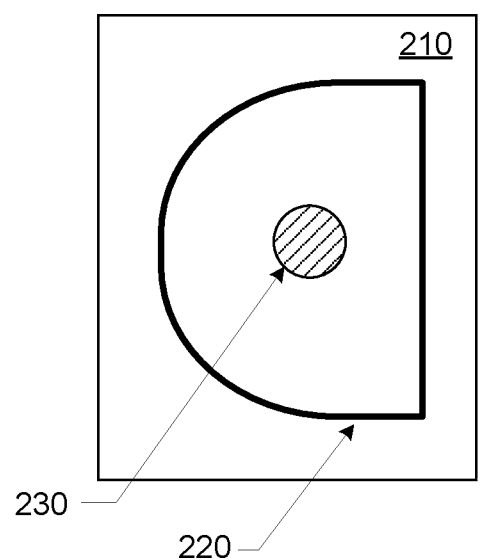
FIG. 2 depicts an exemplary rectangular shaped ostomy appliance with "D"-shaped flange, in accordance with some embodiments of the present invention.

Accordingly, and with reference to FIG. 2, the outer material 210 may be in any shape. Indeed, it is known that nurses, patients, and users often cut or trim this outer material to a desirable shape or size. However, round flanges on ostomies in the prior art prevent location of the appliance directly proximate to a crease, roll, or fold.

FIG. 2 shows an appliance or faceplate with a substantially D-shaped flange 220 mounted on a square or rectangular material 210. Again, an orifice 230 is positioned inside the flange 220 to receive a stoma.

Figure 3:
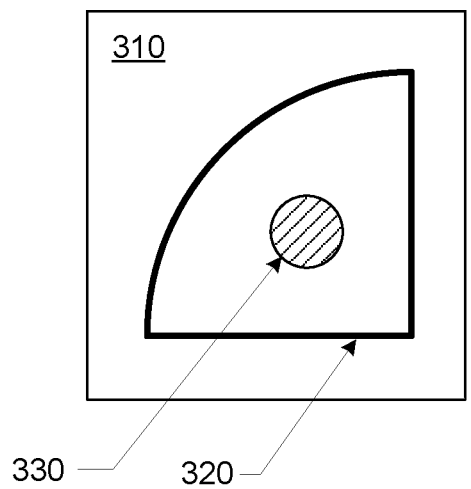
FIG. 3 depicts an exemplary rectangular shaped ostomy appliance with pie-piece shaped flange, in accordance with some embodiments of the present invention.
Figure 4:
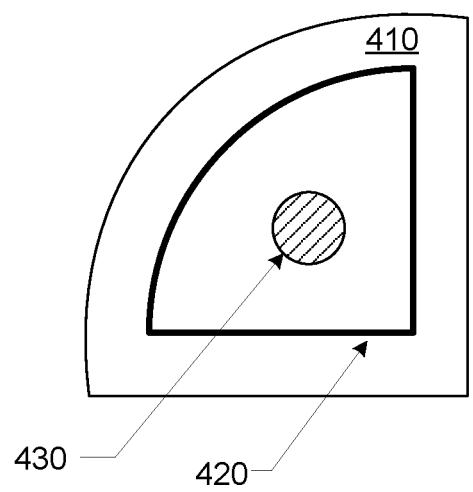
FIG. 4 depicts an exemplary pie-piece shaped ostomy appliance with a pie-piece shaped flange, in accordance with some embodiments of the present invention.
Figure 5:
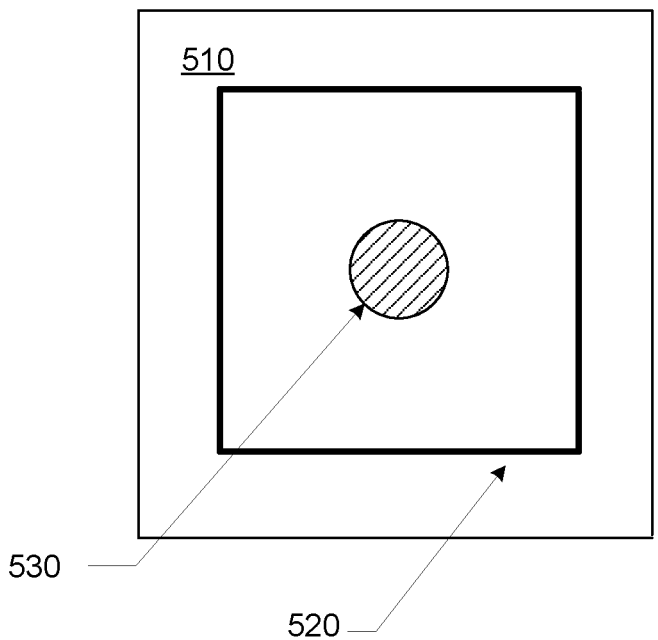
FIG. 5 depicts an exemplary rectangular or polygon-shaped ostomy appliance with a corresponding rectangular or polygon-shaped flange, in accordance with some embodiments of the present invention.

The present invention is intended to address a need in the art of different shaped ostomy appliances or faceplates to accommodate different body types and needs. For example, a user may have a centerline incision due to certain medical procedures (such as, but not limited to, emergency trauma surgery). The user may also have creases, rolls, or folds. To accommodate the centerline wound (and any negative pressure wound device that may be used to assist in closing and healing of the centerline incision) and a user's body type that may include creases, rolls, or folds, there may be more than one substantially straight edge to the flange on the ostomy appliance or faceplate. With reference to FIGS. 3 and 4, a pie-piece shaped flange 320, 420 may be mounted on a softer material 310, 410 which may be of different shapes. The flange 320, 420, may again encircle an orifice 330, 430 for receiving a stoma.

Figure 6:
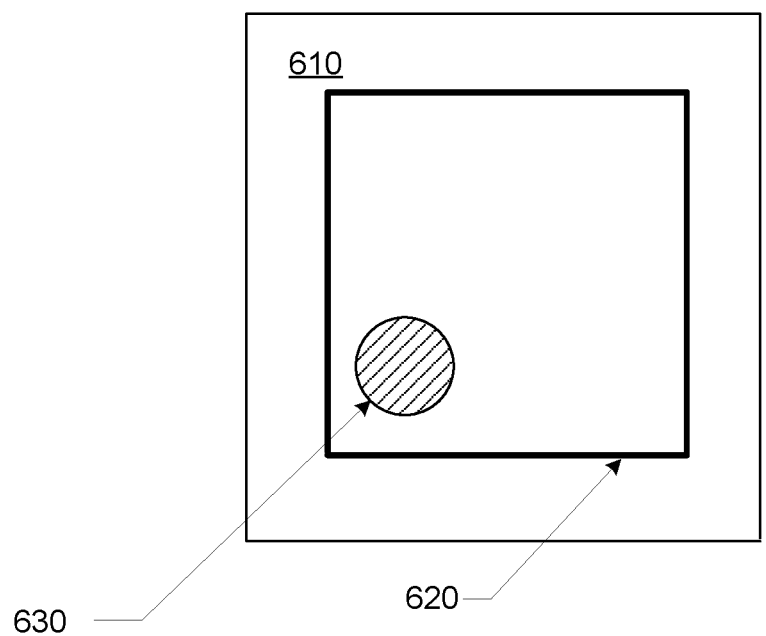
FIG. 6 depicts an exemplary rectangular or polygon-shaped ostomy appliance with a corresponding rectangular or polygon-shaped flange with the aperture for a stoma being positioned asymmetrically inside the flange, in accordance with some embodiments of the present invention.

Similar to FIGS. 3 and 4, FIGS. 5 and 6 present an ostomy appliance with a substantially square or rectangular shaped flange 520, 620, mounted on a softer material 510, 610. Note that it is contemplated by the present invention that the orifice for the stoma may not be centrally located, but may be positioned asymmetrically within the flange. With reference to FIG. 6, the orifice 630 is shown to be positioned in a corner of the flange 620. A user may cut the orifice in the faceplate or appliance to position the orifice in a position necessary to receive a stoma, while aligning the straight or substantially straight edges of the flange with a user's creases, rolls, folds, incisions, wounds, etc.

Figure 7:
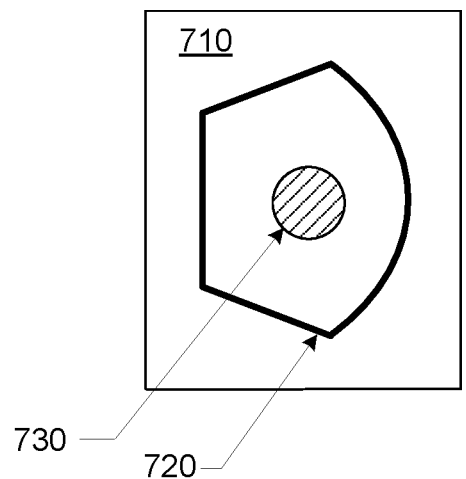
FIG. 7 depicts an exemplary rectangular or polygon shaped ostomy appliance with flange, in accordance with some embodiments of the present invention.
Figure 8:
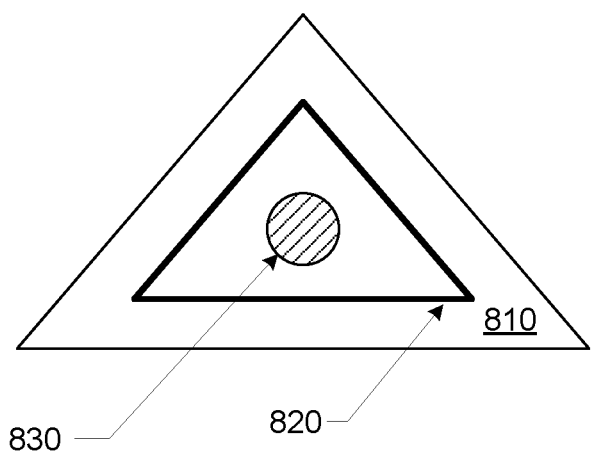
FIG. 8 depicts an exemplary triangular shaped ostomy appliance with a triangular shaped flange, in accordance with some embodiments of the present invention.

The overall shape of the flange can vary, provided that there is at least one straight or substantially straight edge. For example, FIG. 7 illustrates an ostomy appliance with a first material 710, a flange 720, and an orifice 730, in which the flange 720 has several straight and a curved edge. FIG. 8 shows a triangular shaped appliance, comprising a triangular shaped material 810 and a triangular shaped flange 820, including an orifice 830.

Figure 9:
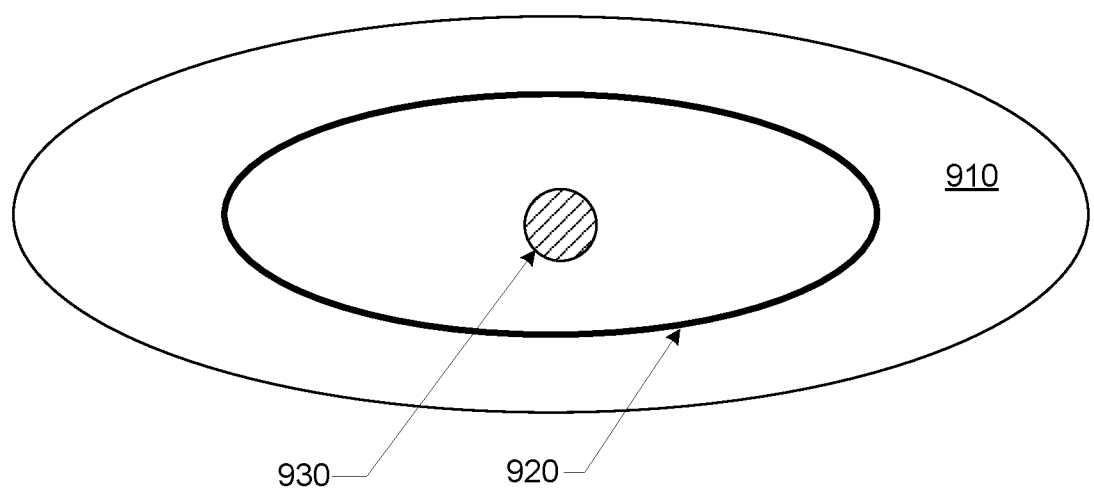
FIG. 9 depicts an exemplary oval-shaped ostomy appliance with an oval-shaped flange, in accordance with some embodiments of the present invention.

Note that while the present invention continually discusses straight or substantially straight edges to the flange, it is understood that some creases, rolls, or folds, may be in the shape of an arc. For example, a fold due to an enlarged abdomen may appear linear, but three-dimensionally may have a curve to it. FIG. 9 shows an oval-shaped ostomy appliance 910 with an oval-shaped flange 920. Again, an orifice 930 is positioned within the flange 920.

Figure 10:
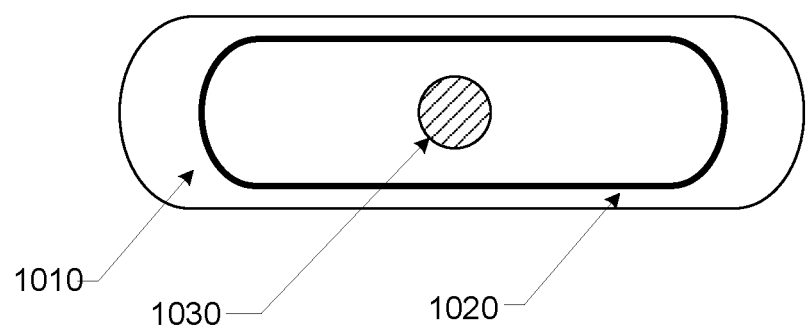
FIG. 10 depicts an exemplary ostomy appliance with flange, in accordance with some embodiments of the present invention.

FIG. 10 shows a rectangular shaped ostomy appliance 1010 and flange 1020, with substantially parallel, substantially straight edges connected by rounded corners. Again, orifice 1030 is positioned within the flange 1020.

Figure 11:
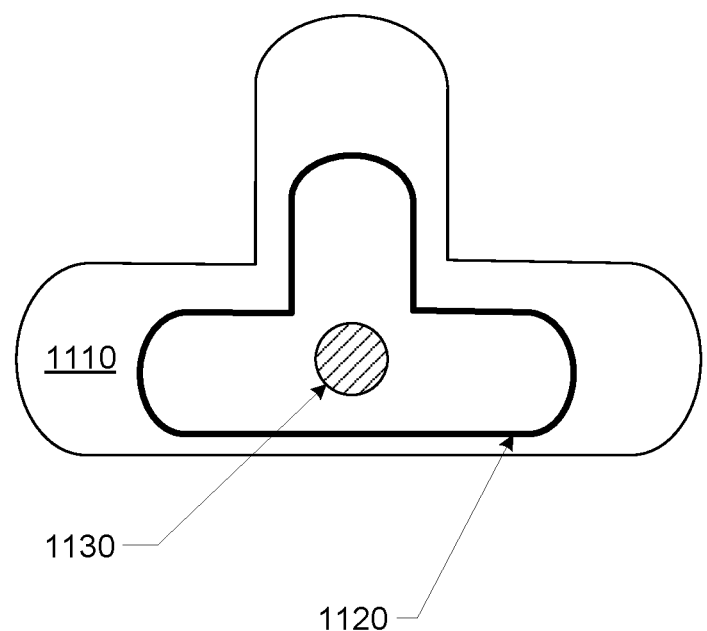
FIG. 11 depicts an exemplary ostomy appliance with flange, in accordance with some embodiments of the present invention.
Figure 12:
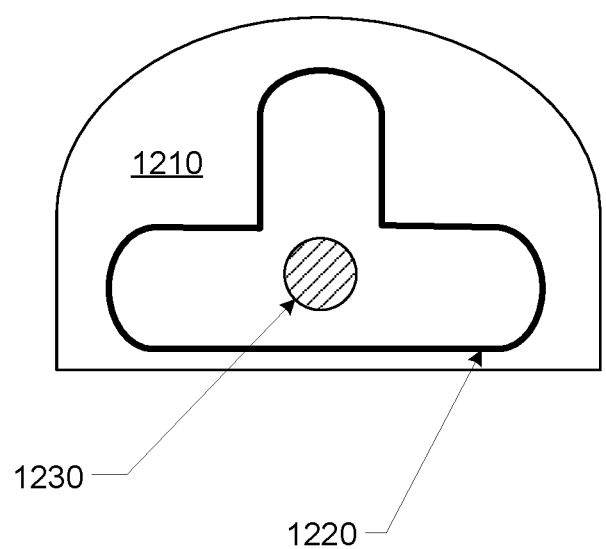
FIG. 12 depicts an exemplary ostomy appliance with flange, in accordance with some embodiments of the present invention.

FIGS. 11 and 12 illustrate an ostomy appliance and flange that may have a more complex shape. FIGS. 11 and 12 illustrates an ostomy appliance 1110, 1210 with a flange 1120, 1220 within which is an orifice 1130, 1230. The overall shape of the flange 1120, 1220 is substantially "T" shaped (though illustrated as an inverted "T").

Figure 13:
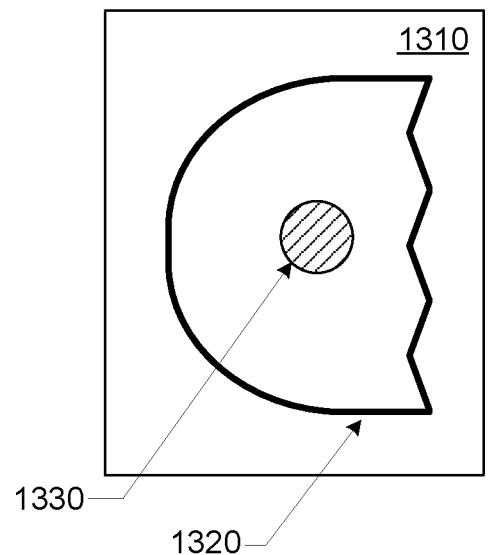
FIG. 13 depicts an exemplary ostomy appliance with flange, in accordance with some embodiments of the present invention.
Figure 14:
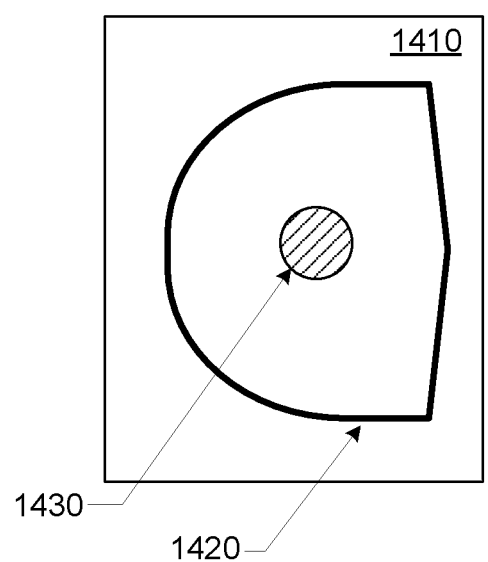
FIG. 14 depicts an exemplary ostomy appliance with flange, in accordance with some embodiments of the present invention.
Figure 15:
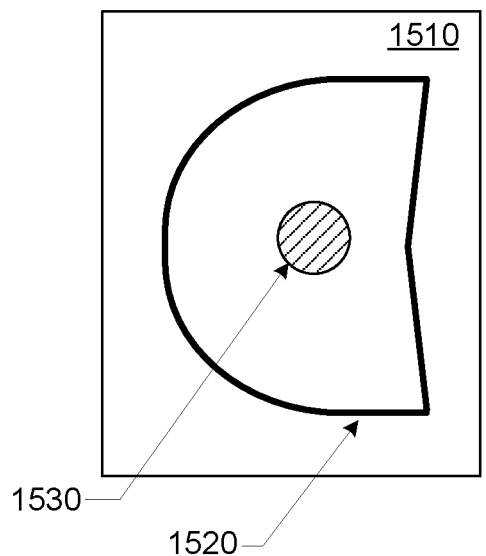
FIG. 15 depicts an exemplary ostomy appliance with flange, in accordance with some embodiments of the present invention.
Figure 16:
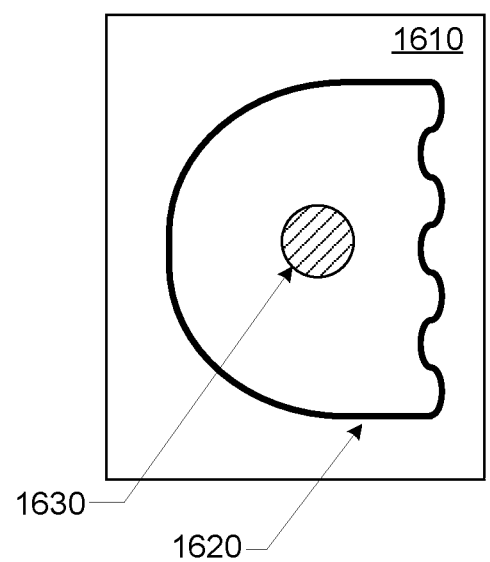
FIG. 16 depicts an exemplary ostomy appliance with flange, in accordance with some embodiments of the present invention.

FIGS. 13-16 illustrate the point that a "substantially straight edge" may include angle (such as in FIGS. 13-15) or curves (such as in FIG. 16). Each appliance includes a first material 1310, 1410, 1510, 1610, a flange 1320, 1420, 1520, 1620, and an orifice 1330, 1430, 1530, 1630. In FIG. 13, the substantially straight edge of the flange 1320 may comprise multiple angled lines. In FIG. 14, the substantially straight edge of the flange 1420 may comprise an angle extending away from the inside of the flange 1420, while in FIG. 15 the substantially straight edge may comprise an angle extending toward the inside of the flange 1520. FIG. 16 illustrates an appliance 1610 with a flange 1630 with a substantially straight edge comprising a series of curves or arcs.

In other words, each embodiment of the ostomy appliance may comprise a flange that has an edge configured to be placed or disposed along an incision, roll, crease, or fold, thereby providing significant advantages over an ostomy appliance with a traditionally round flange.

It will be understood that the specific embodiments of the present invention shown and described herein are exemplary only. Numerous variations, changes, substitutions and equivalents will now occur to those skilled in the art without departing from the scope of the invention. Accordingly, it is intended that all subject matter described herein and shown in the accompanying drawings be regarded as illustrative only, and not in a limiting sense.

What is claimed is:

1. An ostomy appliance being a wafer, barrier, or faceplate, with a flange for mechanical attachment of a bag or pouch, the flange comprising at least one substantially straight edge.

2. The ostomy appliance of claim 1, wherein the flange is substantially "D"-shaped.

3. The ostomy appliance of claim 1, wherein the flange is substantially pie-piece shaped.

4. The ostomy appliance of claim 1, wherein the flange is substantially square shaped.

5. The ostomy appliance of claim 1, wherein the flange is substantially quadrilateral shaped.

6. The ostomy appliance of claim 1, wherein the flange is substantially triangular shaped.

7. The ostomy appliance of claim 1, further comprising an orifice configured to receive a stoma.

8. The ostomy appliance of claim 7, wherein the orifice is disposed asymmetrically within the flange.

9. The ostomy appliance of claim 1, wherein the ostomy appliance or faceplate is comprised of an impermeable, substantially impermeable, or vapor permeable material.

\* \* \* \* \*